United States Patent [19]

Farrell et al.

[11] Patent Number: 4,620,841
[45] Date of Patent: Nov. 4, 1986

[54] PORCELAIN FUSED TO METAL DENTAL SHADE GUIDE

[76] Inventors: Frank C. Farrell; Margaret P. Farrell, both of 18402 N. 70th Dr., Peoria, Ariz. 85345

[21] Appl. No.: 686,098

[22] Filed: Dec. 24, 1984

[51] Int. Cl.⁴ ............................................. A61C 19/10
[52] U.S. Cl. ..................................................... 433/26
[58] Field of Search ......................................... 433/26

[56] References Cited
U.S. PATENT DOCUMENTS
2,765,534 10/1956 Bloom et al. ......................... 433/26

FOREIGN PATENT DOCUMENTS
169093 10/1951 Austria ................................. 433/26

Primary Examiner—Robert Peshock
Attorney, Agent, or Firm—Harry M. Weiss; David G. Rosenbaum

[57] ABSTRACT

A dental shade guide, to be employed by the dentist and dental laboratory technician, to be used in comparing patient's natural teeth for color more accurately. The dental shade guide has plurality of arms or bars constructed of a dental alloy and has corresponding opaque and dental glass fired onto each arm or bar, with each arm or bar varying in color. The same materials used to construct porcelain crowns or bridges is used to construct the dental shade guide.

20 Claims, 6 Drawing Figures

PORCELAIN FUSED TO METAL DENTAL SHADE GUIDE

BACKGROUND OF THE INVENTION

I. Field of the Invention

This invention relates generally to coloration guides for use in dentistry. More particularly, this invention relates to improvements in dental shade guides for use by dentists and dental laboratory technicians. Dental shade guides are used to compare the coloration and shading of artificial teeth for accurate matching with a patient's natural teeth shade and color. The present invention provides a novel dental shade guide which uses the same or similar materials which are used to fabricate dental crowns, artificial teeth or other dental prostheses.

II. Description of the Prior Art

Dental shade guides are an important part of the dental field as a means of communicating a color of a patient's natural teeth from dentist to dental laboratory technician.

Conventional shade guides consist of artificial teeth that are mounted on one end of an individual arm or bar that is marked for that particular shade and then inserted into a plastic holder indicating that shade. This technique can create problems by the fact that the indivual arms or bars can become loose and fall out of the holder and become misplaced.

The artificial teeth of the dental shade guides are almost always manufactured out of a different type of porcelain than the dental glass used to fabricate crowns or bridges, and are fired in a kiln at a much higher temperature than the dental glass to achieve their color.

The thickness of the artificial teeth also causes a problem. The artificial teeth of dental shade guides are 3.5 to 4 millimeters thick and have no metal backing behind them. The dental laboratory technician has to construct a metal frame over a prepared tooth or teeth with a layer of opaque and then a layer of dental glass fired onto the metal all in a confined space of 2 millimeters or less in most cases.

The lack of a metal backing on the conventional dental shade guides renders the color and shade matching with the patient's natural teeth very difficult and often inaccurate. The crown or bridge which will ultimately replace the patient's natural teeth consists of an underlying metal framework covered with opaque. Dental glass is then fired onto the metal thereby creating an oxide layer between the metal and opaque. The artificial tooth having the metal framework, opaque, dental glass and oxide matrix reflects incoming light rather that transmitting it through the tooth as occurs with the non-metal backed artificial teeth of conventional shade guides. This property of light transmission or reflection alters the color and shade of the tooth. Therefore, the shade of an artificial tooth without a metal backing will differ from the shade of and artificial tooth having a metal backing. It is apparent, therefore, that a dental shade guide having a metal backing more accurately represents the true coloration and shading of the artificial teeth, crowns or bridges actually placed in a patient's mouth.

Known prior art examples of dental shade guides are disclosed in U.S. Pat. Nos. 1,518,608; 2,805,478; 3,964,167; and 785,992. These patents exhibit different dental shade guides which are revelant to applicant's invention. Each of these dental shade guides has deficiencies of the types aforementioned in that they do not provide the dentist or dental laboratory technician with a realistic dental shade guide to be used to compare artificial teeth to a patient's natural teeth for color as accurately as possible.

SUMMARY OF THE INVENTION

Accordingly, it is an object of the present invention, which will be described subsequently in greater detail, to provide a realistic dental shade guide, enabling the dentist and dental laboratory technician to accurately compare artificial teeth to a patient's natural teeth Another object of the present invention is to provide a metal blank with attached arms or bars, each arm or bar being opaqued and built up with dental glass having varying colors and shades on each arm or bar.

A further object of the present invention is to provide a dental shade guide which accurately matches the coloration and shading of a patient's natural teeth by using the same or similar materials used to fabricate the crown or bridge placed in the patient's mouth.

It is yet another object of this invention to fabricate a dental shade guide, and will incorporate all the characteristics of a dental glass to metal backed crown or bridge, to be used in determining the particular shade of an artificial tooth, that will be compatible with the patient's natural teeth, by using the materials and methods that are used in fabricating a crown or bridge.

It is still another object of this invention to provide a dental shade guide that has no moveable or removeable parts that can be lost.

It is an alternate object of the present invention to provide a removable shade guide wherein dental glass is fired onto a metal arm or bar.

Other objects and advantages of the present invention will become evident with the accompanying description in conjunction with the drawings.

BRIEF DESCRIPTION OF THE DRAWINGS

The description herein makes reference to the accompanying drawing wherein reference numerals refer to like parts throughout several views, and wherein.

DESCRIPTION OF THE PREFERRED EMBODIMENT

Figure 1:
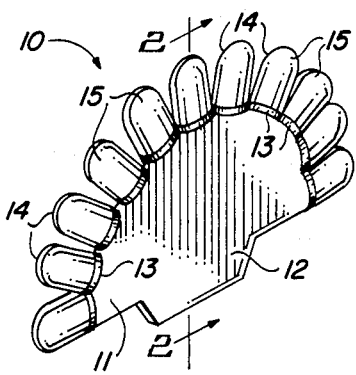
FIG. 1 is a front elevation of the dental shade guide embodying the principles of the present invention completed.
Figure 3:
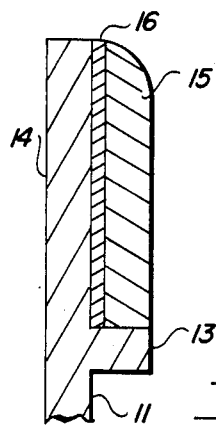
FIG. 3 shows a fragmentary vertical side elevation of a single tooth.
Figure 4:
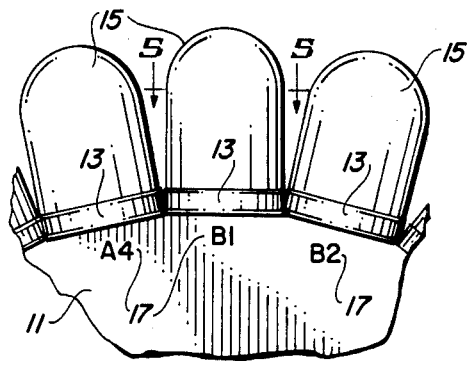
FIG. 4 shows a fragmentary front elevation of the present invention.
Figure 6:
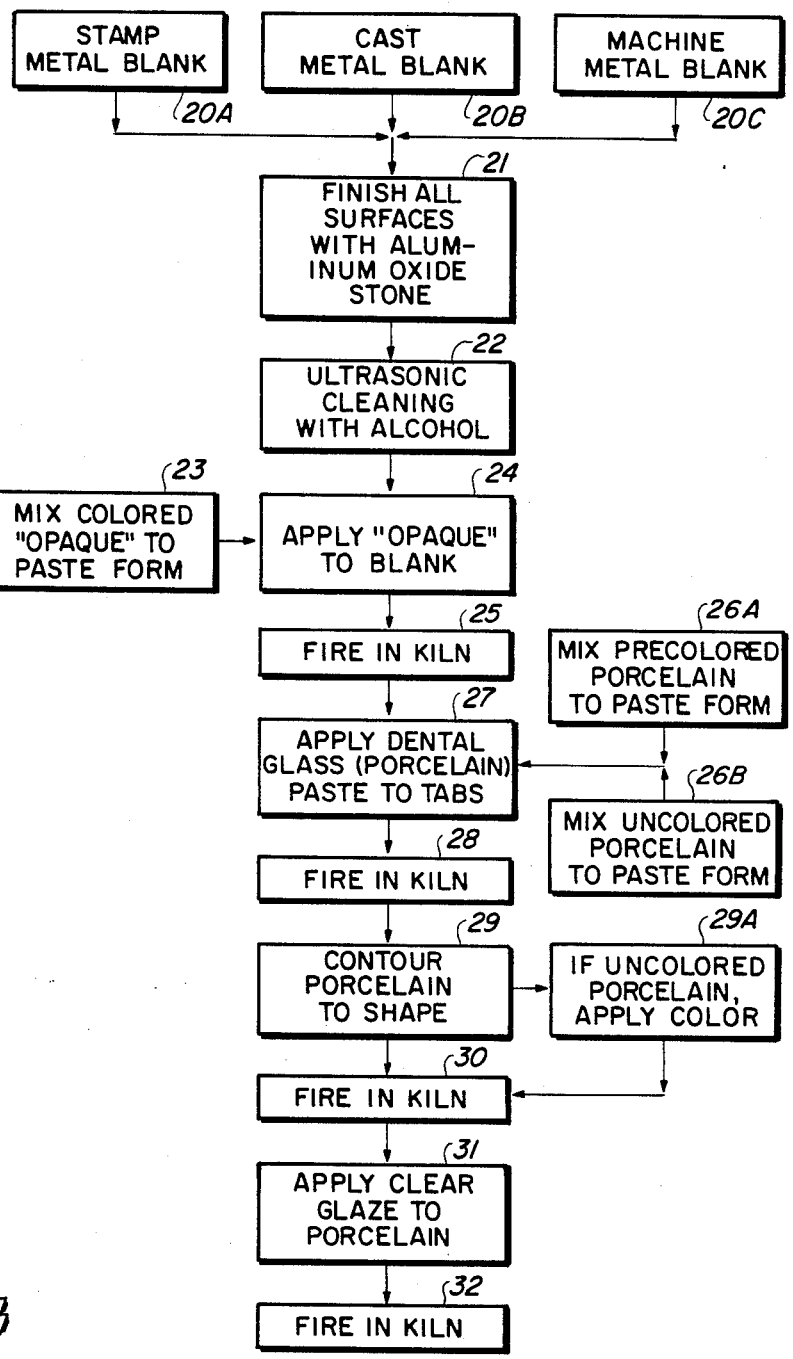
FIG. 6 shows a metal chart of how present invention is constructed.
Figure 5:
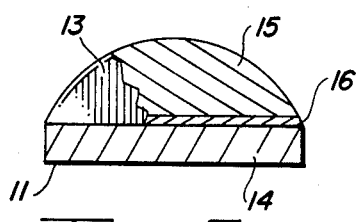
FIG. 5 shows a top plan view of a single tooth.

Referring now in detail to the drawings, FIG. 1 represents the improved dental shade guide to be used for comparing artificial teeth to a patient's natural teeth for color. The metal blank 11 as shown in FIG. 1 is constructed of a dental alloy, the same alloy that is used to fabricate crowns and bridges, which consists of a tab 12 to hold onto the shade guide as shown in FIGS. 1 and 2, and a plurality of arms or bars 14 as shown in FIGS. 1,2,3 and 5, each arm or bar has a separation between them S as shown in FIG. 4, each arm or bar has a collar 13 as shown in FIGS. 1,2,3,4 and 5 to be used as a guideline for applying the opaque 16 and then building up the dental glass 15 to the desired thickness as shown in FIGS. 3 and 5, each arm or bar is opaqued 16 and built up with dental glass 15 in corresponding colors, with each arm or bar varying in color and being given a shade number 17 as shown in FIG. 4.

The plurality of arms or bars 14 may be contiguous with tab 12 and non-removable, or alternatively, arms or bars 14 may be removable (not shown).

The metal blank for the present invention can be stamped out 20A, cast 20B or machine made 20C. Next each arm or bar 14 is finished with aluminum oxide stone 21 to eliminate surface contamination, then cleaned in alcohol in an ultrasonic cleaner 22. Color coded opaque is mixed to a paste form 23 and applied to arm or bar 24, each arm or bar 14 is opaqued 16 with a specific shade, then the metal blank is fired in a vacuumed chamber kiln 25 at an appropriate temperature and for a sufficient time to fuse the opaque to the metal backing. Next the dental glass 15 of a corresponding shade to the opaque is mixed to a paste form 26A, or mix the uncolored dental glass to paste form 26B, apply dental glass paste to tabs 27, each arm or bar 14, if using colored dental glass, is built up with a specific shade. Then the metal blank is fired in a vacuumed chamber kiln 28 at an appropriate temperature and for a sufficient time to fuse the dental glass to the opaque and metal backing. Next the dental glass is contoured to shape 29 then if uncolored porcelain was used apply color 29A, each arm or bar will be colored a specific shade. Then the metal blank is fired in a kiln 30 at an appropriate temperature and for a sufficient time to fuse the porcelain to the dental glass. Then a clear glaze is applied to each arm or bar 31 and then fired in a kiln 32 to a specified temperature.

Figure 2:
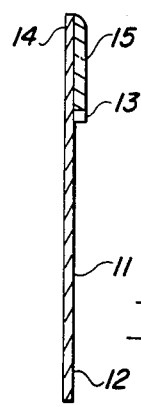
FIG. 2 is a vertical sectional view of the structure taken on line 2—2 of FIG. 1.

Further in another illustration of the invention the metal blank is relatively thin as shown in FIG. 2.

While the above description contains many specificities, these should not be constructed as limitations on the scope of the invention, but rather as an exemplification of a preferred embodiment thereof. Other variations are possible, for example a removeable shade guide fabricated out of dental glass fired to a metal backed arm or bar. Accordingly, the scope of the invention should be determined not by the embodiment illustrated, but by the appended claims and their legal equivalents.

Having thus described the invention, I claim:

1. A dental shade guide for accurately matching the color and shade of a patient's natural teeth, comprising:
    a metal blank;
    a plurality of metal bars affixed to said metal blank, said plurality of metal bars further comprising any suitable dental alloy commonly used in the manufacture of dental prostheses;
    a layer of any suitable opaque material firmly fused to one end of each of said plurality of metal bars and disposed so that said layer of opaque material is entirely backed by said end of each of said plurality of metal bars;
    a layer of any suitable dental glass firmly fused onto said layer of opaque material; and
    a layer of any suitable clear glaze firmly fused onto said layer of porcelain.

2. The dental shade guide according to claim 1, wherein said layer of dental glass is of a suitable thickness to correspond to the amount of dental glass commonly used to fabricate actual dental prostheses.

3. The dental shade guide according to claim 1, wherein said dental glass is contoured.

4. The dental shade guide according to claim 1, wherein said plurality of arms are firmly affixed to said metal blank.

5. The dental shade guide according to claim 1, wherein said plurality of arms are each removably affixed to said metal blank.

6. The dental shade guide according to claim 1, wherein said opaque material comprises a plurality of colors and shades to correspond to a natural range of coloration and shading of teeth.

7. The dental shade guide according to claim 6, wherein said plurality of colors and shades are individually numbered on said metal blank.

8. The dental shade guide according to claim 1, wherein said opaque material, said dental glass and said porcelain is fused by firing in a kiln as a suitable temperature and for a sufficient period of time to permit said fusing.

9. The dental shade guide according to claim 1, wherein each of said plurality of arms of said metal blank further comprises collar means for facilitating accurate disposition of said opaque material and for supporting said layer of dental glass.

10. A method of manufacturing a dental shade guide for accurately matching the color of a dental prosthesis to the color of a patient's natural teeth, comprising the steps of:
    forming a metal blank having a plurality of arms;
    finishing said metal blank to eliminate surface contamination;
    cleaning said metal blank;
    mixing any suitable colored opaque material to a paste form;
    applying said opaque material to each of said plurality of arms of said metal blank;
    firing said opaque material in a kiln at a suitable temperature and for a suitable period of time to fuse said opaque material to each of said plurality of arms of said metal blank;
    applying a layer of dental glass paste onto said fused opaque material;
    firing said dental glass paste in a kiln at a suitable temperature and for a suitable period of time to fuse said dental glass paste onto said fused opaque material;
    contouring said layer of dental glass material to any suitable shape;
    applying any suitable clear glaze onto said layer of fused contoured dental glass; and
    firing said clear glaze in a kiln at any suitable temperature and for a sufficient time to fuse said clear glaze onto said fused contoured dental glass.

11. The method of manufacturing a dental shade guide according to claim 10 wherein said forming of said metal blank further comprises stamping said metal blank.

12. The method of manufacturing a dental shade guide according to claim 10, wherein said forming of said metal blank further comprises casting said metal blank.

13. The method of manufacturing a dental shade guide according to claim 10, wherein said forming of said metal blank further comprises machining said metal blank.

14. The method of manufacturing a dental shade guide according to claim 10, wherein said finishing of said metal blank further comprises finishing with an aluminum oxide stone.

15. The method of manufacturing a dental shade guide according to claim 10, wherein said cleaning of said metal blank further comprises ultrasonic cleaning with alcohol.

16. The method of manufacturing a dental shade guide according to claim 10, wherein said dental glass is pre-colored.

17. The method of manufacturing a dental shade guide according to claim 10, wherein said dental glass is uncolored.

18. The method of manufacturing a dental shade guide according to claim 17, wherein said contouring step further comprises the steps of:
  applying any suitable color to said uncolored dental glass; and
  firing said color onto said uncolored dental glass material at a suitable temperature and for a suitable period of time to fuse said color onto said uncolored dental glass.

19. The method of manufacturing a dental shade guide according to claim 10, wherein said firing steps further comprise firing in a vacuum chamber kiln.

20. The method of manufacturing a dental shade guide according to claim 10, wherein each of said plurality of arms of said metal blank are removable.

* * * * *